US010773063B2

(12) United States Patent
Kimchy et al.

(10) Patent No.: US 10,773,063 B2
(45) Date of Patent: Sep. 15, 2020

(54) DRUG DELIVERY CAPSULE

(71) Applicant: CHECK-CAP LTD., Isfiya (IL)

(72) Inventors: Yoav Kimchy, Haifa (IL); Avner Elgali, Kochav Yair (IL); Dmitry Gubich, Kiryat Motzkin (IL)

(73) Assignee: CHECK-CAP LTD, Isfiya (IL)

(*) Notice: Subject to any disclaimer, the term of this patent is extended or adjusted under 35 U.S.C. 154(b) by 344 days.

(21) Appl. No.: 15/575,386

(22) PCT Filed: May 2, 2016

(86) PCT No.: PCT/IL2016/050451
§ 371 (c)(1),
(2) Date: Nov. 20, 2017

(87) PCT Pub. No.: WO2016/193964
PCT Pub. Date: Dec. 8, 2016

(65) Prior Publication Data

US 2018/0154124 A1 Jun. 7, 2018

Related U.S. Application Data

(60) Provisional application No. 62/272,729, filed on Dec. 30, 2015, provisional application No. 62/168,827, filed on May 31, 2015.

(51) Int. Cl.

| | |
|---|---|
| ***A61M 31/00*** | (2006.01) |
| ***A61B 5/06*** | (2006.01) |
| ***A61B 5/07*** | (2006.01) |
| ***A61B 5/00*** | (2006.01) |
| ***A61K 9/48*** | (2006.01) |

(Continued)

(52) U.S. Cl.
CPC ........... *A61M 31/002* (2013.01); *A61B 5/061* (2013.01); *A61B 5/065* (2013.01); *A61B 5/07* (2013.01); *A61B 5/073* (2013.01); *A61B 5/4839* (2013.01); *A61K 9/0097* (2013.01); *A61K 9/4808* (2013.01); *A61M 31/00* (2013.01); *A61N 1/327* (2013.01); *A61B 2562/0247* (2013.01); *A61M 2205/3303* (2013.01)

(58) Field of Classification Search
CPC ......... A61B 5/073; A61B 5/061; A61B 5/065; A61B 1/041; A61M 31/002; A61K 9/0097
See application file for complete search history.

(56) References Cited

U.S. PATENT DOCUMENTS

| | | | | |
|---|---|---|---|---|
| 2004/0068204 A1* | 4/2004 | Imran | A61B 5/0538 | 600/593 |
| 2004/0253304 A1* | 12/2004 | Gross | A61B 1/041 | 424/451 |

(Continued)

FOREIGN PATENT DOCUMENTS

| | | |
|---|---|---|
| EP | 2201938 A1 | 6/2010 |

*Primary Examiner* — Nathan R Price
*Assistant Examiner* — Anh Bui
(74) *Attorney, Agent, or Firm* — Soroker Agmon Nordman

(57) ABSTRACT

A delivery capsule configured to be swallowed to deliver medication inside the gastrointestinal tract, including a pressure sensor for measuring the internal pressure in the delivery capsule; one or more compartments for storing medication; and a controller configured to control the release a dose of medication from a compartment responsive to the measurements of the pressure sensor.

18 Claims, 5 Drawing Sheets

190
191
192
100
195
105
194
193
199
160
160
130
140
100
155
150
135
185
125
185
180
175
170
120
185
155
145
125
185
110
115
195

(51) Int. Cl.
*A61K 9/00* (2006.01)
*A61N 1/32* (2006.01)

(56) References Cited

U.S. PATENT DOCUMENTS

| | | | | |
|---|---|---|---|---|
| 2004/0267240 | A1 | 12/2004 | Gross et al. | |
| 2005/0192478 | A1 | 9/2005 | Williams et al. | |
| 2007/0161885 | A1 | 7/2007 | Kimchy | |
| 2011/0160129 | A1 | 6/2011 | Imran | |
| 2013/0345505 | A1* | 12/2013 | Trovato | A61B 5/411 600/104 |
| 2014/0001047 | A1* | 1/2014 | Kahn | A61B 5/14546 204/426 |

* cited by examiner 190
191
192
100
195
105
194
193
160
160
130
140
100
155
150
135
185
125
185
175
180
170
120
185
155
145
125
185
110
115
199
195

DRUG DELIVERY CAPSULE

RELATED APPLICATIONS

This application claims priority under 35 U.S.C. 120 from US provisional application No. 62/168,827 dated May 31, 2015 and US provisional application No. 62/272,729 dated Dec. 30, 2015, the disclosures of which are incorporated herein by reference.

FIELD OF THE DISCLOSURE

The present disclosure relates generally to the delivery of medication and more specifically to delivery of medication with a swallowable capsule.

BACKGROUND OF THE DISCLOSURE

The delivery of medication directly to specific locations in the gastrointestinal (GI) tract, for example to the small intestine and the colon, has the potential of improving the therapeutic properties in applying a wide range of drugs. For example drug release to specific locations can be used to effectively treat inflammatory bowel diseases such as colitis and crone disease.

Generally the therapeutic performance of drugs that are provided orally are degraded by enzymes in the stomach and by being diluted until reaching the desired location thus reducing their effectiveness.

Methods known in the art to deliver medication to the small intestine and colon after traversing the stomach suggest use of microspheres and slow release polymers that rely on physiological attributes of the gastrointestinal tract such as pH changes from the stomach to the small intestine, bacteria presence in the colon vs. the small intestine, time dependent release and pressure dependent release. These methods have been tested with various degree of success but none of these methods has proved to be a reliable and repetitive method for delivering drugs to the small intestine or colon and ensuring that the drug is indeed released in the small intestine or colon.

In recent years the use of an imaging capsule has been developed to examine the gastrointestinal tract for the existence of polyps and other clinically relevant features that may provide an indication regarding the potential of cancer. This is performed by swallowing an imaging capsule that is durable in the gastrointestinal tract so that the imaging capsule can travel through the gastrointestinal tract and view a patient's situation from within at desired locations. In a typical case the trip can take between 24-48 hours after, after which the imaging capsule exits in the patient's feces. Typically the patient swallows a contrast agent to enhance the imaging ability of the imaging capsule. Then the patient swallows the imaging capsule to examine the gastrointestinal tract while flowing through the contrast agent. The imaging capsule typically includes a radiation source, for example including a radioisotope that emits X-rays and/or Gamma rays. The radiation typically may be collimated to allow it to be controllably directed toward a specific area during the imaging process. In an exemplary case the imaging capsule is designed to measure X-Ray fluorescence and/or Compton back-scattering and transmit the measurements (e.g. count rate, particle energy) to an external analysis device, for example a transceiver worn by the patient and/or a computer or other dedicated instruments.

U.S. Pat. No. 7,787,926 dated Aug. 31, 2010 and U.S. Pat. No. 9,037,219 dated May 19, 2015 both by the current applicant, the disclosures of which are incorporated herein by reference, describe details related to the manufacture and use of such an imaging capsule.

Optionally, an imaging capsule with or without imaging ability can be used to traverse the gastrointestinal tract and reach specific locations. If the capsule is designed to identify its position and to release medication at the specific location then it can be used for delivering medication.

SUMMARY OF THE DISCLOSURE

An aspect of an embodiment of the disclosure, relates to a delivery capsule for controllably delivering medication in the gastrointestinal tract. The delivery capsule includes means for determining its location in the gastrointestinal tract. The delivery capsule releases medication when the capsule reaches selected locations, for example when entering the colon or after an hour from entering the colon.

In an exemplary embodiment of the disclosure, the means for determining the location of the capsule includes a pressure sensor that measures the pressure inside the delivery capsule. Alternatively or additionally, the means include a gas detection component that can for example identify a concentration level of Hydrogen in the delivery capsule. Further alternatively or additionally, the means include an external location system that is deployed on the body of the patient that swallowed the delivery capsule. Optionally, the external location system may determine the location of the delivery capsule based on the detection of radiation emitted from the delivery capsule. Alternatively, the location may be determined based on electromagnetic transmissions, for example low frequency transmissions.

In some embodiments of the disclosure, the delivery capsule includes a controller that determines when to commence releasing medication and when to cease releasing medication. Optionally, the capsule may take measurements and transmit them to an external transceiver or computer either directly or indirectly. Optionally, the external transceiver or computer may analyze the measurements and provide instructions to the delivery capsule, for example when to release medication. Optionally, the instructions may include a list of locations for releasing medication.

There is thus provided according to an exemplary embodiment of the disclosure, a delivery capsule configured to be swallowed to deliver medication inside the gastrointestinal tract, comprising:

a pressure sensor for measuring the internal pressure in the delivery capsule;

one or more compartments for storing medication; and a controller configured to control the release a dose of medication from a compartment responsive to the measurements of the pressure sensor.

In an exemplary embodiment of the disclosure, the controller records the measurements of the pressure sensor, analyzes them and determines a location of the delivery capsule inside the gastrointestinal tract based on the measurements. Alternatively or additionally, the delivery capsule comprises a transceiver for communicating with an external device; and wherein the delivery capsule communicates the measurements of the pressure sensor to an external device to analyze the measurements and determine the location of the delivery capsule. In an exemplary embodiment of the disclosure, the delivery capsule further includes an imaging system to form images of its surrounding location and is configured to release medication in response to analysis of the images. Optionally, the delivery capsule is configured to provide a list of locations for releasing medication by a subsequently swallowed capsule. In an exemplary embodiment of the disclosure, the delivery capsule is configured to release medication upon entering a specific organ. Alternatively or additionally, the delivery capsule is configured to release medication at a preselected time after entering a specific organ. Optionally, the delivery capsule includes a gas detection component that detects a level of concentration of gas and controls the release of medication also in response to the level of concentration of the gas. In an exemplary embodiment of the disclosure, the delivery capsule receives an external notification of the location of the delivery capsule and controls release of medication by taking into account also the location from the external notification. Optionally, the delivery capsule is programed to release medication at different locations relative to a prior swallowed delivery capsule. In an exemplary embodiment of the disclosure, the delivery capsule releases medication synchronously with pressure waves sensed by the pressure sensor. Optionally, the delivery capsule includes external electrodes that are provided with current to create electroporation when releasing medication.

There is further provided according to an exemplary embodiment of the disclosure, a method of controlling the release of medication by a delivery capsule, comprising:

introducing into the gastrointestinal tract a delivery capsule with a pressure sensor;

measuring the pressure within the delivery capsule as it traverses the gastrointestinal tract;

analyzing the pressure measurements to determine the current location of the delivery capsule;

instructing a controller in the delivery capsule to control the release of medication from a compartment in the delivery capsule responsive to the analysis of the pressure measurements.

In an exemplary embodiment of the disclosure, the controller records the measurements of the pressure sensor, analyzes them and determines a location of the delivery capsule inside the gastrointestinal tract based on the measurements. Alternatively or additionally, the delivery capsule comprises a transceiver for communicating with an external device; and wherein the delivery capsule communicates the measurements of the pressure sensor to an external device to analyze the measurements and determine the location of the delivery capsule. In an exemplary embodiment of the disclosure, the delivery capsule further includes an imaging system to form images of its surrounding location and is configured to release medication in response to analysis of the images. Optionally, the delivery capsule is configured to provide a list of locations for releasing medication by a subsequently swallowed capsule. In an exemplary embodiment of the disclosure, the delivery capsule is configured to release medication upon entering a specific organ. Alternatively or additionally, the delivery capsule is configured to release medication at a preselected time after entering a specific organ. In an exemplary embodiment of the disclosure, the delivery capsule includes a gas detection component that detects a level of concentration of gas and controls the release of medication also in response to the level of concentration of the gas.

BRIEF DESCRIPTION OF THE DRAWINGS

The present disclosure will be understood and better appreciated from the following detailed description taken in conjunction with the drawings. Identical structures, elements or parts, which appear in more than one figure, are generally labeled with the same or similar number in all the figures in which they appear, wherein.

DETAILED DESCRIPTION

Figure 1:
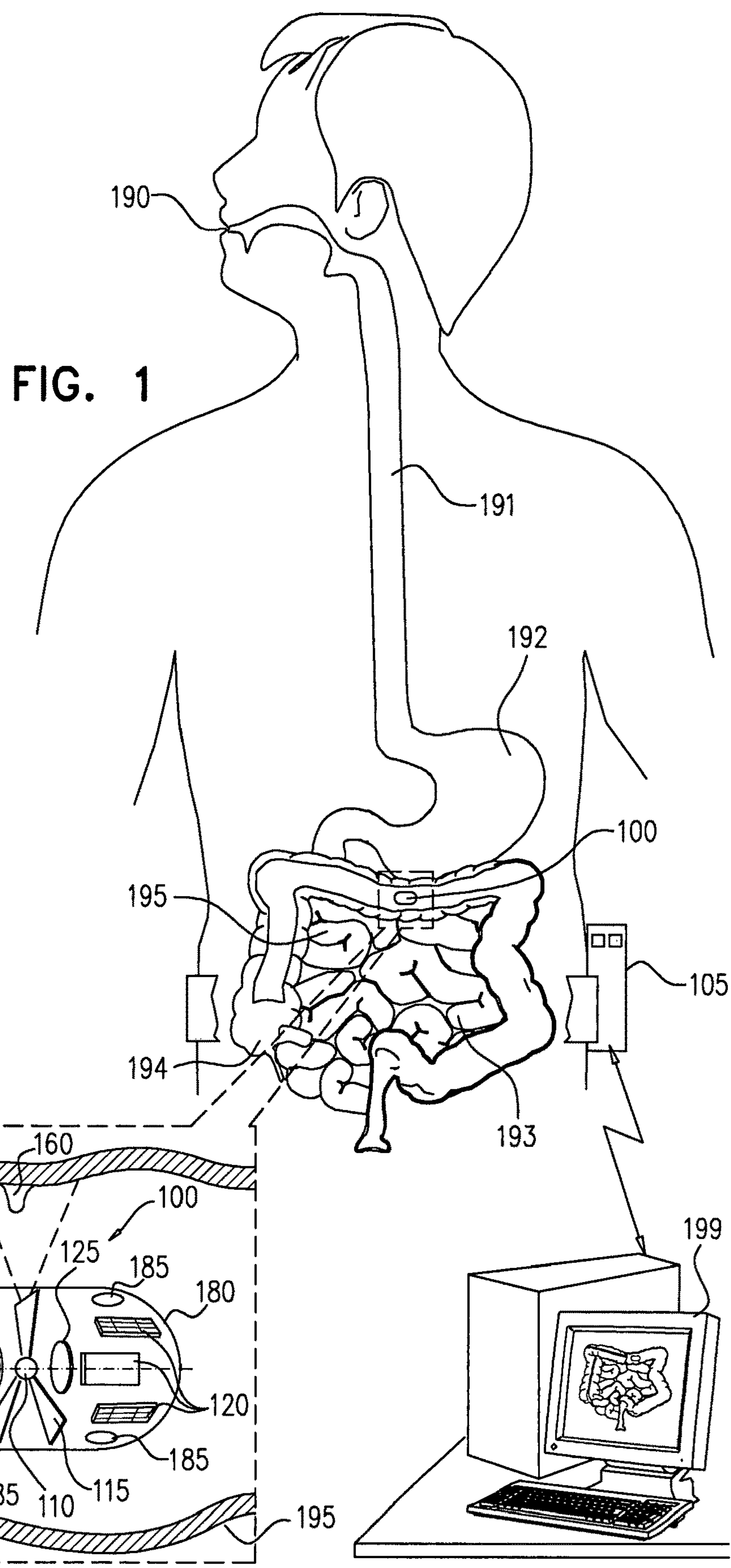
FIG. 1 is a schematic illustration of a delivery capsule deployed in a patient's colon, according to an exemplary embodiment of the disclosure.

FIG. 1 is a schematic illustration of a delivery capsule 100 deployed in a patient's colon 195, according to an exemplary embodiment of the disclosure. Optionally, delivery capsule 100 is designed to identify its location and deliver medication to selected locations. In some embodiments of the disclosure, delivery capsule 100 can also serve to scan the location with radiation to form images of the gastrointestinal tract. Optionally, delivery capsule 100 includes the elements described below to enable it to perform this task. Alternatively, delivery capsule 100 only serves to identify its location and deliver medication and does not include some of the elements described below.

In an exemplary embodiment of the disclosure, if delivery capsule 100 is also used to acquire images then the patient first swallows a radio opaque contrast agent solution (e.g. based on Barium or Iodine). The radio opaque contrast agent solution mixes with the content of the gastrointestinal tract to increase the accuracy in detecting cancerous tissue based on measurements taken from inside the patient's body. After swallowing the radio opaque contrast agent solution the patient swallows the delivery capsule 100. In an exemplary embodiment of the disclosure, the delivery capsule 100 travels through the patient's mouth 190, esophagus 191, stomach 192, small intestine 193 and then enters the cecum 194, which is the beginning of the colon 195. The delivery capsule 100 then travels through the colon and exits through the rectum and anus. In an exemplary embodiment of the disclosure, the delivery capsule 100 is able to identify its location, for example that it has entered the colon 195 and then the delivery capsule 100 will begin scanning by releasing radiation to form images from inside the colon 195. Optionally, the delivery capsule 100 can release radiation at any location along the gastrointestinal tract, for example in the small intestine 193 or in the stomach 192 to acquire images at those locations. Optionally, delivery capsule may analyze the images in real-time to determine if to release medication or not, for example near a polyp or other abnormality. Alternatively or additionally, the delivery capsule 100 may only release medication at specific locations and not acquire images.

In some embodiments of the disclosure, instead of storing the measurements and analyzing them internally the measurements are provided to an external transceiver 105 that is worn by the user and stored for analysis, for example stored on a memory card (e.g. SD card) that can be extracted and analyzed by a computer 199 to construct images from the measurements. Alternatively or additionally, the external transceiver 105 stores and analyzes the measurements. Further alternatively or additionally, the measurements may be transmitted directly from the delivery capsule 100 to the computer 199 or transmitted to the external transceiver 105 and then provided to the computer 199 in real-time. Optionally, the delivery capsule 100, external transceiver 105 and/or computer 199 act in real-time to instruct the delivery capsule to release medication and/or release radiation to acquire additional images.

In an exemplary embodiment of the disclosure, delivery capsule 100 comprises an encasement 180 shaped as an elongated cylinder with an elongated axis and having flat or spherically shaped ends. Alternatively, other shapes may be used, for example a parallelepiped having flat ends, pyramid shaped ends or other shapes. In an exemplary embodiment of the disclosure, delivery capsule 100 includes an outlet 170 for releasing medication on demand. In an exemplary embodiment of the disclosure, delivery capsule 100 may include multiple compartments 175 each containing a dose of medication. Upon receiving an instruction each compartment 175 releases in turn a dose of fluid or powder through outlet 170. Alternatively or additionally, delivery capsule 100 may employ other mechanisms to release doses of medication, for example an electromechanical release mechanism, a piston, a striking pin, a pump and the like.

In an exemplary embodiment of the disclosure, delivery capsule 100 includes a radiation source 110 that emits X-Ray or gamma radiation and is optionally positioned at the center of a collimator 115 (e.g. a circular/cylindrical collimator) to control the direction of emission of radiation from the radiation source 110. In an exemplary embodiment of the disclosure, the delivery capsule 100 controls the release of radiation through the collimators, so that the delivery capsule 100 can block the emission of radiation or unblock the emission of radiation in addition to controlling its direction. Optionally, the radiation source is also located between two radiation blocking disks 125 (e.g. cylindrical tungsten disks) to prevent emission of radiation from the upper and lower ends of the delivery capsule 100.

In an exemplary embodiment of the disclosure, the delivery capsule 100 further includes any of the following: one or more radiation detectors 120, a power source 150 (e.g. a battery), a controller 130 optionally having a processor and memory to analyze the measurements initiate communications and provide instructions, a pressure sensor 135 and a transceiver 140 for communicating with an external transceiver 105 or computer 199 to receive instructions and provide measurements/images.

In an exemplary embodiment of the disclosure, the elements of the delivery capsule 100 (e.g. 120, 130, 135 140, 150) are connected electronically and/or physically to enable the delivery capsule 100 to function correctly, for example the detectors 120 detect the energy levels of particles emitted responsive to radiation emitted by the radiation source and provide the information to controller 130 and/or transceiver 140.

In an exemplary embodiment of the disclosure, pressure sensor 135 may be a high sensitivity pressure sensor such as LPS25H from STmicrosystems or a similar element.

In an exemplary embodiment of the disclosure, the colon 195 may include cancerous or non-cancerous polyps/tumors 160 for example as shown in FIG. 1. Optionally, as delivery capsule 100 traverses the colon it radiates the inner walls of the colon 195 with X-Ray and gamma radiation. In response detectors 120 of delivery capsule 100 detect particles (e.g. photons, electrons) responding to the emitted radiation. Optionally, delivery capsule 100 forms a count for each energy level representing the number of particles having the specific energy level resulting from Compton backscattering and X-Ray fluorescence. These measurements are then analyzed to form images of the insides of the colon 195 or other organs. In some embodiments of the disclosure, delivery capsule 100 may release medication upon detection of a polyp or other abnormality at the location of detection. Alternatively or additionally, delivery capsule 100 may record coordinates of the location (e.g. on computer 199) and use them to provide medication when swallowing another delivery capsule 100.

In some embodiments of the disclosure, the delivery capsule 100 may include a light source and a standard imaging chip (e.g. CMOS or CCD). Optionally, the capsule may shine light as it progresses through the gastrointestinal tract (e.g. the small intestine 193) and release medication based on the images that are obtained.

In an exemplary embodiment of the disclosure, encasement 180 is mostly made up from a rigid material such as Polycarbonate with windows 185 optionally covered by a softer material, for example silicon or thermoplastic elastomers (TPE), adhering to the rigid material. Optionally, the softer material is pushed in or pushed out in response to a difference in the pressure inside the delivery capsule 100 relative to the pressure outside the delivery capsule 100 in the different organs of the patient (e.g. stomach 192, small intestine 193 or colon 195). Optionally, when the softer material is pushed inward the volume of the delivery capsule 100 decreases and the pressure increases. In an exemplary embodiment of the disclosure, pressure sensor 135 identifies the change in the pressure from inside the delivery capsule 100 and uses it to determine the location of the capsule (e.g. in which organ it is currently located or if it is at the beginning or end of the organ).

Figure 2:
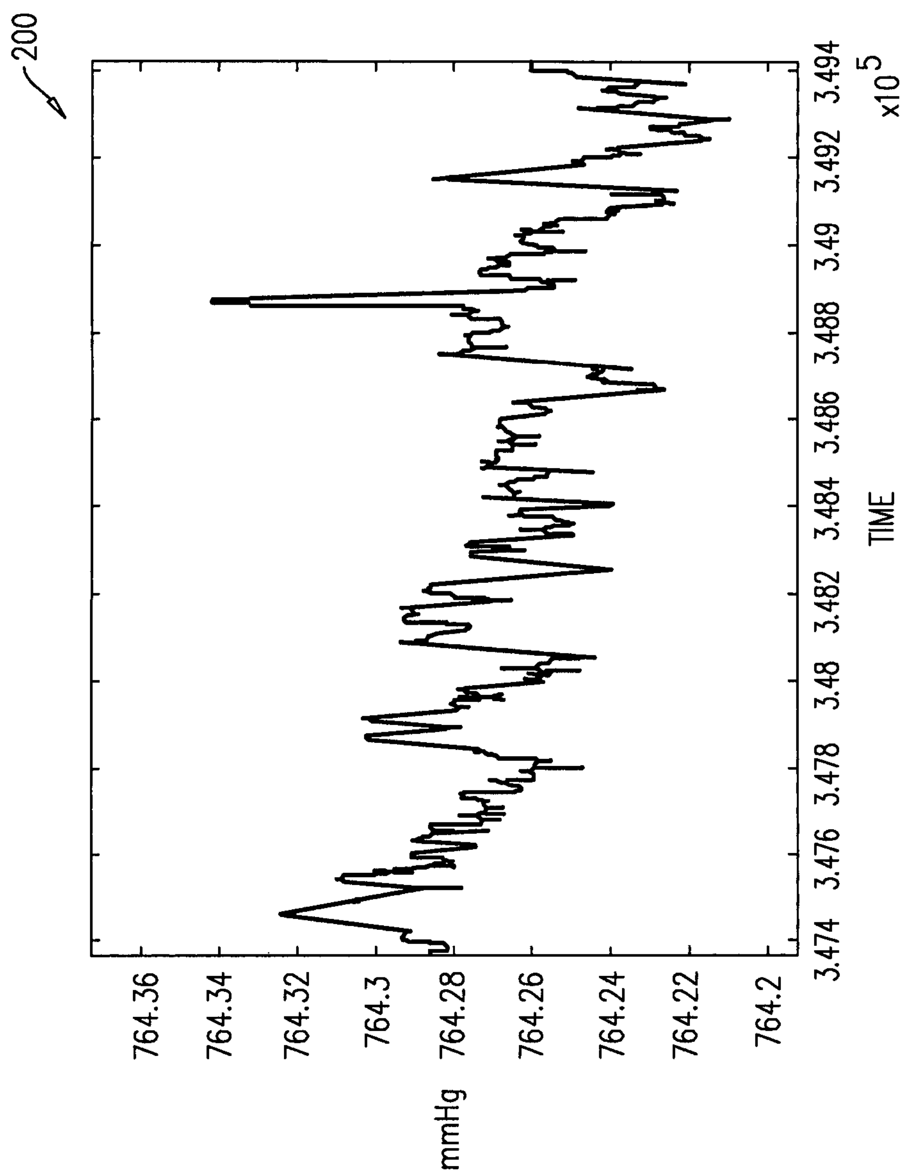
FIG. 2 is a schematic illustration of a graph of typical pressure waves in the small intestine, according to an exemplary embodiment of the disclosure.
Figure 3:
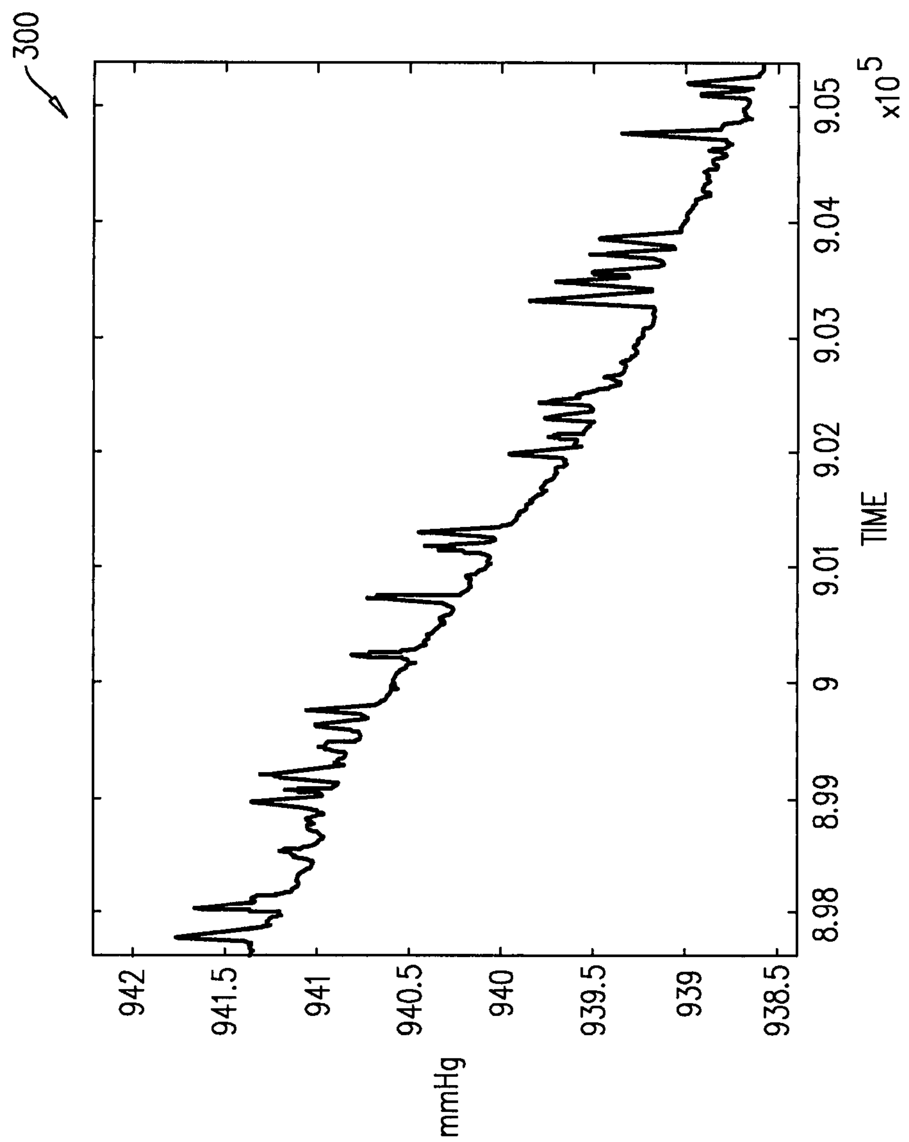
FIG. 3 is a schematic illustration of a graph of typical pressure waves in the colon, according to an exemplary embodiment of the disclosure.

In an exemplary embodiment of the disclosure, the pressure measured by pressure sensor 135 is due to forces applied by the muscles of the small intestine 193, colon 195 and/or other organ. Alternatively or additionally, the pressure measured is due to hydrostatic pressures in each organ, for example from the content and pressure on the content. Optionally, the hydrostatic pressure in the colon 195 causes pressure waves with a duration of a few seconds to a few tens of seconds in contrast to a different timing in the small intestine 193. In an exemplary embodiment of the disclosure, pressure waves in the small intestine 193 are typically of the order of 1-20 mmHg in contrast to pressure waves in the colon, which are typically of the order of 20-100 mmHg. Optionally, the difference in hydrostatic pressure is used to differentiate between the locations of the delivery capsule 100. In an exemplary embodiment of the disclosure, the frequency of the pressure waves is used to distinguish between the small intestine 193, the colon 195 and other organs, for example pressure waves in the small intestine 193 tend to be regular with a typical time interval of 15-20 seconds between the pressure waves. In contrast in the colon the interval between pressure waves tends to be random (e.g. irregular) with typical time intervals of a few minutes to a few hours between pressure waves. FIG. 2 is a schematic graph 200 of typical pressure waves in the small intestine 193 and FIG. 3 is a schematic graph 300 of typical pressure waves in the colon 195.

In an exemplary embodiment of the disclosure, gases can penetrate the encasement 180 of delivery capsule 100. Optionally, the gases penetrate by diffusion into the delivery capsule 100 at a rate that is dependent on the material of the encasement 180. For example a rigid material such as polycarbonate enables slower diffusion than silicon.

In an exemplary embodiment of the disclosure, the gas diffusion causes the internal pressure of the delivery capsule 100 to gradually rise with the hydrostatic pressure and muscle pressure causing relatively small fluctuations around the internal pressure due to the diffusion. Initially, the pressure inside the delivery capsule 100 is about 1 atmosphere (760 mmHg) and the pressure increases while traversing the gastrointestinal tract. Optionally, the gastrointestinal tract includes $CO_2$, Methane ($CH_4$), $H_2$ and other gases which are generally dissolved or generated by the contents in the colon 195. The contents of the colon 195 include a large number of bacteria of different types and species that release $H_2$, Methane, $CO_2$ and other gases during their metabolic processes. The bacteria reside mainly in the colon and much less in the small intestine 193. Therefore, the presence of these gases is mainly confined to the colon 195. Optionally, the pressure in the colon 195 is about 100-250 mmHg greater than 1 atmosphere, depending on the size, weight and posture of the patient. This difference in pressure induces the gases to diffuse into the delivery capsule 100 at a faster rate than in the small intestine 193. In an exemplary embodiment of the disclosure, diffusion starts once the delivery capsule 100 is swallowed and increases from the stomach 192 to the small intestine 193 and further increases in the cecum 194 and colon 195. Generally, the diffusion is relatively limited in the stomach 192 and the small intestine 193, but increases substantially when the delivery capsule 100 enters the colon 195 due to the presence of bacteria in the colon 195. Optionally, in the small intestine 193 the delivery capsule 100 is engulfed by small tissue with almost no content in contact with the capsule, therefore only small amounts of gas molecules diffuse through the walls of the delivery capsule 100. However when the delivery capsule 100 enters the cecum 194 a large amount of content with a lot of dissolved gas is in contact with the delivery capsule 100 and the influx of gas molecules into the delivery capsule 100 is increased sharply to equalize the pressure inside the delivery capsule 100 with the surrounding content.

Figure 4:
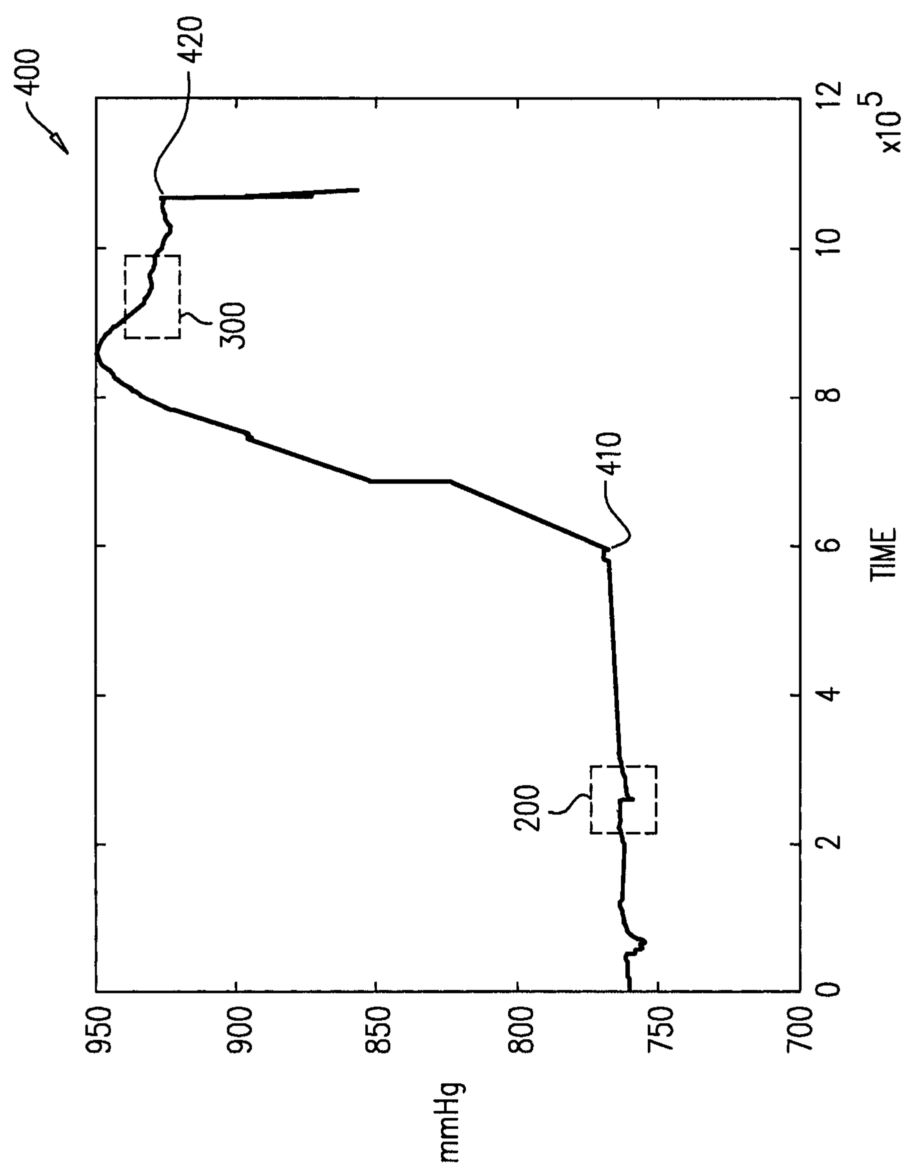
FIG. 4 is a schematic illustration of a graph showing a typical increase in internal pressure over time due to gas diffusion, according to an exemplary embodiment of the disclosure.
Figure 5:
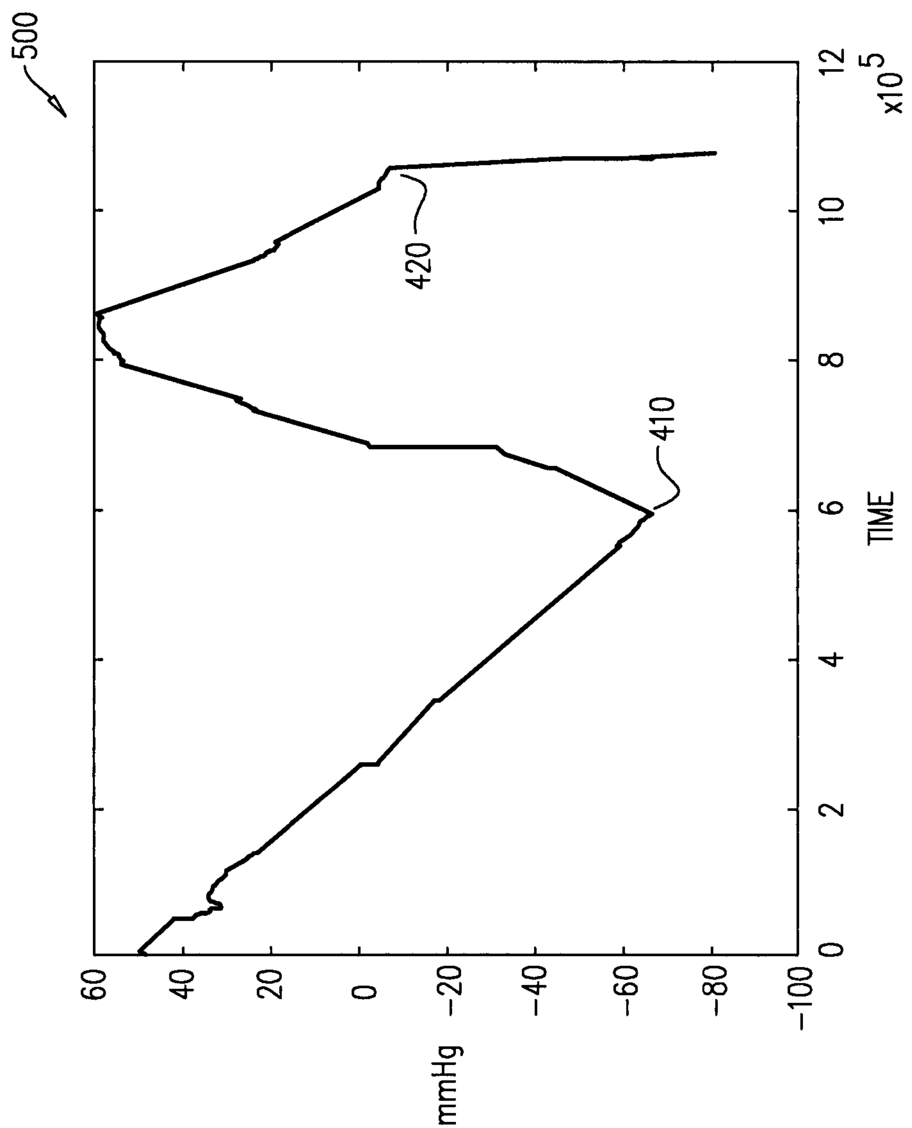
FIG. 5 is a schematic illustration of a graph of a simple de-trend of the graph showing a typical increase in internal pressure over time due to gas diffusion, according to an exemplary embodiment of the disclosure.

In an exemplary embodiment of the disclosure, pressure sensor 135 records an increase in the pressure as more gas enters the capsule by diffusion. FIG. 4 is a schematic illustration of a graph 400 showing a typical increase in internal pressure over time due to gas diffusion. Optionally, graph 200 is an enlarged view of the earlier stage in graph 400, depicting fluctuations of pressure of the delivery capsule 100 in the small intestine 193 and graph 300 is an enlarged view of a later stage of graph 400 depicting the pressure in the delivery capsule 100 in the colon. FIG. 5 is a schematic illustration of a graph 500 showing a simple de-trend of the graph in FIG. 4 emphasizing the inflection points of internal capsule pressure, for example point 410 as the delivery capsule 100 enters the colon 195 and point 420 when the delivery capsule 100 exits the anus.

In an exemplary embodiment of the disclosure controller 130 uses the above details to determine the location of the delivery capsule 100, for example if it is in the stomach 192, the small intestine 193, the colon 195 or in the beginning or end of each organ. Alternatively, the recorded information (e.g. pressure measurements) are transmitted to external transceiver 105 and analyzed there or transmitted from there to computer 199 for analysis. Optionally, the analysis is performed in real-time so that delivery of medication and/or radiation scanning may be started or stopped in response to the measurements and determinations made based on the analysis (e.g. when entering the colon or exiting the colon or rectum). Optionally, external transceiver 105 or computer 199 notify the capsule to release medication and/or to commence or cease radiating based on the location of the delivery capsule 100 determined from the analysis.

In an exemplary embodiment of the disclosure, analysis of the pressure measurements are performed continuously or periodically. Optionally, during analysis the previous calculations (at an earlier time) are verified based on the new measurements to differentiate between pressure fluctuations inside a specific organ and transition into a different organ. Optionally, controller 130 includes a timer so that delivery capsule 100 may be configured to start releasing medication and/or radiating at a pre-selected time after entering a specific organ, for example a few hours after entering the small intestine 193 before it is expected to enter the colon, to be sure to scan the cecum 194 and/or the entire colon 195. Alternatively or additionally, the delivery capsule 100 may be configured to start releasing medication and/or scanning with radiation every time there is an extreme fluctuation in the pressure measurements or a specific pattern is identified by the imaging process, for example to identify and/or release medication at damaged areas or during transition from one organ to another. Optionally, delivery capsule 100 may record and analyze images once entering a specific organ to locate a specific location based on specific patterns and then release medication. For example images from a previous use of a delivery capsule 100 may be provided to delivery capsule 100 (e.g. prior to being swallowed or by wireless communications during a succeeding run). Optionally, in the succeeding run delivery capsule 100 releases medication when locating positions that were selected by a practitioner from the previous run.

In an exemplary embodiment of the disclosure, delivery capsule 100 includes a gas detection component 145 such as marketed by Element One Inc. from Boulder Colo. Gas detection component 145 is designed to detect Hydrogen gas within the delivery capsule 100. Optionally, when delivery capsule 100 is in the colon a high concentration of Hydrogen diffuses into the delivery capsule. Identification of a level of exposure to Hydrogen gas being above a threshold value provides an indication that the capsule has reached the colon 195. In some embodiments of the disclosure, the information from gas detection element 145 is used in addition to the information provided by pressure sensor 135. Alternatively, the information from gas detection element 145 is used instead of the information from pressure sensor 135.

In some embodiments of the disclosure, radiation detectors are placed on the body of the patient to serve as an external tracking system and detect the location of the capsule in real-time based on the radiation emitted by the capsule as described for example in U.S. Pat. No. 7,787,926 dated Aug. 31, 2010. Optionally, when the capsule reaches specific locations, for example the small intestine or the colon, the external transceiver 105 can notify the controller 130 to release or begin to release medication. In an exemplary embodiment of the disclosure, the information provided by the tracking system may be used in addition to the other location detection systems and methods described above (e.g. Hydrogen detection, pressure sensor detection). Optionally, delivery capsule 100 may act based on more than one location determination system, for example releasing medication only when two location determination systems indicate that the delivery capsule is in a specific location/organ (e.g. the colon).

In some embodiments of the disclosure, the external tracking system may be designed to detect the location of the capsule based on electromagnetic signals, for example low frequency electromagnetic transmissions such as described in PCT patent application no: PCT/IL14/50404 filed on May 5, 2014 and published as WO 2014/195934 the disclosure of which is incorporated herein by reference In an exemplary embodiment of the disclosure, the encasement 180 includes electrodes 155 for electroporation providing targeted, localized drug delivery for the treatment of inflammatory or other intestinal disorders. Optionally, power source 150 includes a pulse generator to apply short electric pulses by electrodes 155 to transiently disrupt cell membranes. In an exemplary embodiment of the disclosure, when releasing medication delivery capsule 100 generates an electric charge on electrodes 155 to create electroporation. The electroporation enhances the medication kinetic properties and delivery to the blood stream, for example in the small intestine or colon.

In an exemplary embodiment of the disclosure, the delivery capsule 100 has a diameter of about 10-13 mm (approximately the diameter of the small intestine 193 when not under stress) to provide good mechanical contact between electrodes 155 and the surrounding tissue, for example in the small intestine 193.

In some embodiments of the disclosure, the delivery capsule 100 is designed that the overall specific density is greater than 1 (the specific density of water), for example 2 grams per cm cube so that it sinks better in the content of the colon 195 while traversing through the colon. Optionally, the electrodes 155 on the surface of the delivery capsule 100 achieve better contact with the colon tissue when having a specific density that is greater than the specific density of the standard content of the colon.

In some embodiments of the disclosure, the location detection system determines a relative position along the small intestine and/or the colon, for example based on the increase in pressure, or Hydrogen density. Optionally, the delivery capsule is preprogrammed to deliver medication to a specific position in an organ, for example the middle of the small intestine, ¾ of the way through or near the end. In some embodiments of the disclosure, the delivery capsule is programmed while traversing the gastrointestinal tract, for example based on communications from the external transceiver 105. Optionally, capsules swallowed sequentially can be programmed so that each will deliver medication to different locations to enable tissue at a first location to recuperate from local effects caused by the medication or by the electroporation applied when releasing the medication.

In some embodiments of the disclosure, delivery capsule 100 releases medication and/or applies electroporation signals synchronously with pressure waves sensed by the pressure sensor 135, for example in the small intestine 193 and/or in the colon 195. Generally, pressure waves are sensed when the muscles of the surrounding organ press on the delivery capsule 100. Therefore releasing medication and/or applying electroporation when the pressure waves occur can enhance the transfer of medication into the blood stream at the locations selected for release of medication.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the disclosure. Further combinations of the above features are also considered to be within the scope of some embodiments of the disclosure.

It will be appreciated by persons skilled in the art that the present invention is not limited to what has been particularly shown and described hereinabove. Rather the scope of the present invention is defined only by the claims, which follow.

We claim:

1. A delivery capsule configured to be swallowed to deliver medication inside a gastrointestinal tract, comprising:

a pressure sensor configured to measure an internal pressure in the delivery capsule reflecting a hydrostatic pressure within the delivery capsule due to gas diffusion from outside the delivery capsule into the delivery capsule;

one or more compartments for storing medication; and a controller configured to determine fluctuations in hydrostatic pressure due to gas diffusion, analyze the fluctuation in hydrostatic pressure to determine a location of the delivery capsule inside the gastrointestinal tract and control release of a dose of medication from a compartment responsive to the measurements of the pressure sensor.

2. A delivery capsule according to claim 1, wherein the delivery capsule comprises a transceiver for communicating with an external device; and wherein the delivery capsule communicates the measurements of the pressure sensor to an external device to analyze the measurements and determine the location of the delivery capsule.

3. A delivery capsule according to claim 1, wherein the delivery capsule further includes an imaging system to form images of its surrounding location and is configured to release medication in response to analysis of the images.

4. A delivery capsule according to claim 1, wherein the delivery capsule is configured to provide a list of locations for releasing medication by a subsequently swallowed capsule.

5. A delivery capsule according to claim 1, wherein the delivery capsule is configured to release medication upon entering a specific organ.

6. A delivery capsule according to claim 1, wherein the delivery capsule is configured to release medication at a preselected time after entering a specific organ.

7. A delivery capsule according to claim 1, wherein the delivery capsule includes a gas detection component that detects a level of concentration of gas and controls the release of medication also in response to the level of concentration of the gas.

8. A delivery capsule according to claim 1, wherein the delivery capsule receives an external notification of the location of the delivery capsule and controls release of medication by taking into account also the location from the external notification.

9. A delivery capsule according to claim 1, wherein the delivery capsule is programmed to release medication at different locations relative to a prior swallowed delivery capsule.

10. A delivery capsule according to claim 1, wherein the delivery capsule releases medication synchronously with pressure waves sensed by the pressure sensor.

11. A delivery capsule according to claim 1, wherein the delivery capsule includes external electrodes that are provided with current to create electroporation when releasing medication.

12. A method of controlling the release of medication by a delivery capsule, comprising:

introducing into a gastrointestinal tract a delivery capsule with a pressure sensor;

measuring an internal pressure reflecting a hydrostatic pressure within the delivery capsule due to gas diffusion from outside the delivery capsule into the delivery capsule as it traverses the gastrointestinal tract;

determining fluctuations in hydrostatic pressure due to gas diffusion;

analyzing the fluctuations in hydrostatic pressure to determine a current location of the delivery capsule inside the gastrointestinal tract;

instructing a controller in the delivery capsule to control release of medication from a compartment in the delivery capsule responsive to the analysis of the pressure measurements.

13. A method according to claim 12, wherein the delivery capsule comprises a transceiver for communicating with an external device; and wherein the delivery capsule communicates the measurements of the pressure sensor to an external device to analyze the measurements and determine the location of the delivery capsule.

14. A method according to claim 12, wherein the delivery capsule further includes an imaging system to form images of its surrounding location and is configured to release medication in response to analysis of the images.

15. A method according to claim 12, wherein the delivery capsule is configured to provide a list of locations for releasing medication by a subsequently swallowed capsule.

16. A method according to claim 12, wherein the delivery capsule is configured to release medication upon entering a specific organ.

17. A method according to claim 12, wherein the delivery capsule is configured to release medication at a preselected time after entering a specific organ.

18. A method according to claim 12, wherein the delivery capsule includes a gas detection component that detects a level of concentration of gas and controls the release of medication also in response to the level of concentration of the gas.

* * * * *